United States Patent [19]

Meyrat et al.

[11] Patent Number: 5,015,591
[45] Date of Patent: May 14, 1991

[54] METHOD AND APPARATUS FOR FILTERING AND METERING LIQUID SAMPLES

[75] Inventors: Pierre-André Meyrat; Alain Oppliger, both of La Chaux-de-Fonds; Denis Steiner, St-Imier, all of Switzerland

[73] Assignee: Nivarox-FAR S.A., Switzerland

[21] Appl. No.: 256,523

[22] Filed: Oct. 12, 1988

[30] Foreign Application Priority Data

Oct. 15, 1987 [CH] Switzerland ............... 04036/87

[51] Int. Cl.$^5$ .................... B01L 3/02; G01N 1/14
[52] U.S. Cl. ................... 436/178; 73/864.25; 210/738; 210/767; 210/143; 210/416.1; 210/435; 422/100; 422/101; 422/102; 436/180
[58] Field of Search ........... 210/739, 767, 143, 416.1, 210/435, 445, 450, 483; 422/68, 99, 100, 101, 102; 436/177, 178, 180; 73/864.23, 864.24, 864.25

[56] References Cited

U.S. PATENT DOCUMENTS

| | | | |
|---|---|---|---|
| 3,371,786 | 3/1986 | Fann | 210/90 |
| 3,811,484 | 5/1974 | Engelbrecht | 141/59 |
| 4,219,530 | 8/1980 | Kopp et al. | 422/101 |
| 4,259,291 | 3/1981 | Smythe | 73/864.22 |
| 4,457,184 | 7/1984 | Shiono | 73/864.11 |
| 4,478,095 | 10/1984 | Bradley et al. | 73/864.23 |
| 4,503,012 | 3/1985 | Starr | 422/100 |
| 4,528,158 | 7/1985 | Gilles et al. | 422/100 |
| 4,738,826 | 4/1988 | Harris | 422/100 |
| 4,869,116 | 9/1989 | Meyrat et al. | 73/864.34 |

FOREIGN PATENT DOCUMENTS

2217669 10/1973 Fed. Rep. of Germany .
2609168 7/1988 France .

Primary Examiner—W. Gary Jones
Attorney, Agent, or Firm—Sughrue, Mion, Zinn, Macpeak & Seas

[57] ABSTRACT

The method of filtering and metering a liquid sample set forth herein includes the steps of providing a first recipient (1) in which the sample is placed, the volume of the sample being greater than the quantity to be metered, providing a second recipient (2) into which the sample is decanted in the same proportions, interposing filtering means (7) between the first and second recipients, decanting into the first recipient a quantity of the sample less than the excess quantity contained in the second recipient and providing a third recipient (3) into which is decanted from the second recipient the desired quantity of liquid samples. The method may be employed for example in processing the adenosine triphosphate (ATP) molecule.

9 Claims, 4 Drawing Sheets

METHOD AND APPARATUS FOR FILTERING AND METERING LIQUID SAMPLES

This invention concerns a method and an arrangement for filtering and measuring liquid samples.

BACKGROUND OF THE INVENTION

In order to analyze liquid samples one often requires an apparatus which enables initially filtration of the samples, then metering thereof. Such an apparatus may be used for instance in the measurement of the ATP (adenosine triphosphate) content of a substance in order to be able to estimate the biological activity thereof In an article of the review "Soil Biol. Biochem." volume 16, Nr 4, pages 361-366, 1984, N. Maire describes a method of analysis of a medium such as soil which consists in extracting the ATP molecule from the cells of the medium by rupture of the cell walls, then by the photometric measurement of the molecule by an enzymatic reaction of the bioluminescence, the intensity of the emitted light in the course of this reaction being directly proportional to the concentration of ATP, this concentration itself representing the biological activity of the sample of examined soil. Effectively, ATP is a mononucleotide of metabolism which is found in all living organisms and which assures transmission or stockage of energy reserves in the majority of biochemical reactions taking place at the center of living cells (respiration, fermentation, photosynthesis, etc.).

The extraction of the ATP molecule by rupture of the cell walls is brought about by diluting the soil sample in a certain quantity of acid such as $H_2SO_4$, preferably completed by a mechanical mixing operation of the thus diluted sample. Since furthermore, the enzymatic reaction necessary for the photometric analysis does not withstand an acid medium, it is necessary, before proceeding with the photometric analysis, to adjust the pH to an almost neutral value by addition of a special additive intended to this effect. The adjustment of the pH must naturally take place within a well determined volume of the sample and it is at this level that in the arrangement described hereafter are to be found the essential characteristics of this invention.

It is well understood that the description to follow of this analysis arrangement must not be considered as a limitation to the applications of the invention which, on the contrary, may be employed each time that one wishes to obtain filtering and metering of a certain number of individual samples without there being risk of contamination of the samples among themselves.

Effectively, when one wishes to treat successively a large number of liquid samples with a precise volumetric metering, one is confronted with a problem of rinsing the elements which provide the metering and the ducting which establishes the communication between these various elements.

Generally, the cleaning of a flow circuit of the samples is brought about with a rinsing liquid which washes them between the metering of the successive samples in order to flush all residue of the previously treated sample.

In failing to take this precaution, such residues may modify the characteristics of the following sample such as for instance its composition or its concentration, from which there may well result errors when analysis is undertaken.

Beside the fact that the rinsing operation risks modifying the concentration of the samples, since there remains always within the flow circuit a certain quantity of rinsing liquid, it is necessary likewise to observe that this operation requires special elements and that furthermore it prolongs the treatment time of each sample since during the cleaning operation metering may not take place.

U.S. Pat. No. 4,869,116 describes a method and an apparatus by means of which the metering of successive samples may be brought about without disturbing either the composition or the concentration of the samples and likewise without increasing the time necessary for treating each sample over and beyond the time interval strictly necessary for the metering operation.

In order to obtain this result, the described method consists in preparing in several first recipients samples the volume of which is made up of the quantity of sample desired plus an excess quantity of sample, and successively decanting the contents of each of the first recipients initially towards an outlet up to the amount of the excess quantity, then towards the second recipient until the desired quantity of sample has been obtained. Thus the excess quantity of the following sample is itself employed for rinsing the flow circuit, in flushing from this circuit all residue of the preceding sample, following which the second recipients may receive only a correct quantity of sample exclusively made up of the liquid formed by the following sample.

The abovementioned characteristics are found in the present invention which however proposes an improvement of the method in the sense that filtering of the sample is totally independent of its metering which thus enables a more precise metering. Furthermore, the present invention leads to the proposal of an arrangement less complicated and more universal in its employment.

SUMMARY OF THE INVENTION

The method of the invention comprises the steps of providing a first recipient in which is placed the sample to be filtered and metered, the volume of the sample comprising the desired quantity plus an excess, providing a second recipient into which is decanted the sample contained in the first recipient, the volume decanted likewise comprising the desired quantity plus an excess, interposing filtering means between the first and second recipients, decanting into the first recipient a quantity of sample less than the excess quantity in the second recipient, providing a third recipient into which is decanted from the second recipient the desired quantity of the liquid sample.

The arrangement for carrying out the method of the invention as set forth hereinabove comprises a first filtering station comprising a first recipient containing the liquid sample to be filtered and metered plus a quantity thereof in excess of the desired volume, a second recipient further including means for decanting the sample into said second recipient and filtering means interposed in the decanting circuit, a second metering station located after said first filtering station, said second metering station comprising pumping means for initially discharging into the first recipient a certain quantity of liquid from the second recipient and subsequently discharging into a third recipient a predetermined quantity of liquid from the second recipient corresponding to the desired quantity in response to metering means arranged in the second station.

The invention will be better understood with the help of the description to follow given by way of example and having reference to the attached drawings

DESCRIPTION OF THE PREFERRED EMBODIMENT

Figure 1:
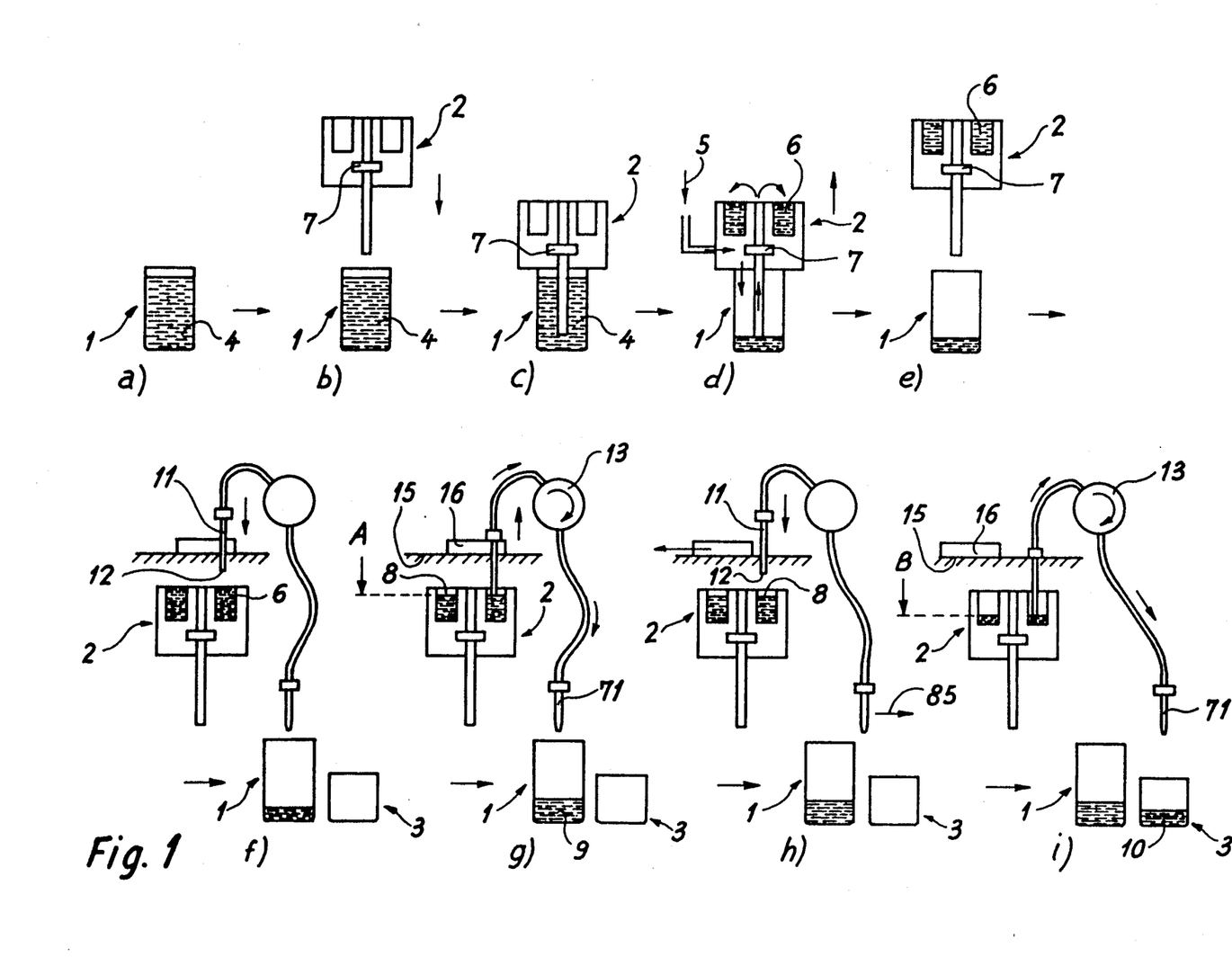
FIG. 1 is a schematic drawing illustrating the general principle of the method and the arrangement proposed by the invention, FIGS. 1a to 1e showing successively the several stages leading to the filtering of the sample and FIGS. 1f to 1i showing successively the various stages leading to the metering of said sample.

FIG. 1 is a schematic drawing illustrating the general principle of the method and of the arrangement proposed by the invention, In FIG. 1 is shown that one provides a first recipient or receptacle 1 containing the sample 4 to be filtered and metered. The volume of this sample is arranged to contain the desired quantity (determined by the metering which is to follow) plus an excess quantity of the sample. In FIG. 1b is shown a second recipient or receptacle 2 into which is decanted the sample contained in the first recipient. A method of decanting is shown in FIG. 1d. In order to bring about the decanting according to the method taken as example, one places the second recipient 2 over the first recipient 1 as shown on FIG. 1c, then one injects compressed air 5 into the first recipient which will drive all or part of the liquid into the second recipient. It is arranged such that the volume of the sample 6 decanted into the second recipient is likewise made up of the desired sample quantity plus an excess quantity.

Methods of decanting other than that which has been shown by way of example hereinabove may be envisaged. For instance the second recipient could be provided with a hollow piston adapted to be introduced into the first recipient which would form a cylinder. By driving it into this recipient the cylinder would thus force the liquid into the second recipient.

In the path followed by the liquid during the decanting one provides, according to the invention, filtering means which are symbolized in FIGS. 1b to 1e by a chamber 7 which may contain a paper filter for instance.

As soon as the filtered liquid is stored in the second recipient 2, one proceeds with the decanting into the first recipient 1 of a quantity of sample 8 less than the excess quantity contained in the second recipient as is apparent on FIG. 1g. One may be sure in this manner that there will remain sufficient liquid for the metering which is to follow. This quantity of sample 8 is chosen to be sufficient however to rinse the ducting of all residues which could remain following treatment of a preceding sample according to the principle evoked hereinabove. It will be noted that the first recipient 1 which had contained the non-filtered sample now serves as a waste receptacle for that quantity of liquid 8 which will not be employed. The contents 9 of the first recipient may then be thrown away.

Following the rinsing, one, finally proceeds with the decanting into a third recipient or receptacle 3 of the quantity of liquid sample desired as shown on FIG. 1i. One thus obtains in the third recipient 3 the desired quantity 10 of the liquid.

The principle of the metering, i.e. of the decanting into the third recipient of a desired quantity of liquid has been thus explained in its most general sense. Several methods may be considered for effecting this metering. One could for instance employ the cylinder-piston system mentioned hereinabove, the piston travel defining the quantity of liquid to be metered. Hereinafter there will be described the preferred method which is a specific characteristic of the invention and which is interesting in view of its simplicity as well as by the precision of the result obtained.

In this method one brings initially the second recipient 2 in line with a pipette 11 as may be seen on figure 1f. Next one plunges the pipette 11 into the liquid 6 and sucks the liquid to the point where it has attained a first level A corresponding to the level of orifice 12 of the pipette. One pours the liquid thus sucked 8 into the first recipient 1 (see FIG. 1g). As is well understood the arrangement is such that the quantity of liquid thus poured off is less than the excess quantity contained in the second recipient 2. This quantity is measured by the depth to which the pipette has been plunged, since as soon as the liquid has attained level A at which is located the orifice of the pipette, no further aspiration of the liquid is possible. As shown on FIG. 1i, one next lowers the orifice 12 of the pipette 11 to a second level B, below the first, chosen in a manner such that the liquid contained between the first level A and the second level B corresponds to the desired quantity of liquid sample to be metered. Finally, one sucks the liquid contained between the two levels A and B and pours it into the third recipient 3. The quantity of liquid desired 10 is thus stored in this latter recipient. There likewise it is understood that the suction of the liquid is interrupted as soon as the liquid has attained level B where the orifice of the pipette is located. The liquid is aspired by means of a pump 13 as shown on FIGS. 1f to 1i. The pump intake is coupled to the pipette 11 and its discharge to another pipette 71 which may be displaced in line with the first recipient 1 or in line with the third recipient 3 in following the path indicated by arrow 85.

The displacement of the orifice of pipette 11 from level A which consists in fact in a zero setting of the system to the level B may be brought about in various manners, for instance in running a motor during a predetermined time or further a stepping motor which could be programmed. Here there has been preferred a system employing a reference plane 15 and a shim 16 as is seen on figures 1f to 1i. Such a system will be described in detail further on.

There will now be described having reference to figures 2 to 5 an arrangement for carrying out the method according to the invention, such method having been set forth hereinabove.

In general, the arrangement according to the invention is intended for treating several liquid samples one after another. The samples contained in the first recipients 1, are placed on a carrousel or a transporting band, the advance of which is regulated as a function of the operations to be performed. Generally, with each first recipient 1 there is associated a third recipient 3 which is to contain at the end of the operations the desired metered quantity of liquid. Generally also, with each pair presented by the first and third recipients, there is associated a second recipient 2 in which is brought about the filtration. These three recipients are transported successively from one work station to the next.

In treating ATP molecules as mentioned hereinabove, one will find at the first station the addition of a predetermined quantity of $H_2SO_4$ to the sample previously poured into the first recipient, at the second station, mixing of the solution obtained at the first station, at the third station, the decanting with filtration of the liquid from the first to the second recipient, at the fourth station, the metering of the liquid and the storing of the metered quantity in the third recipient, at the fifth station, adjustment of the pH of the metered quantity and at the sixth station, photometric analysis of the sample resulting from the operation brought about at the fifth station. These various stations are controlled through interfaces which transform the orders from a computer into control signals utilizable by the various elements equipping the work stations. The computer is generally provided with a screen and a controlling keyboard, the installation functioning automatically with the help of a program which is executed by the computer. The transport band effects an intermittent translation movement likewise controlled by the computer.

Figure 2:
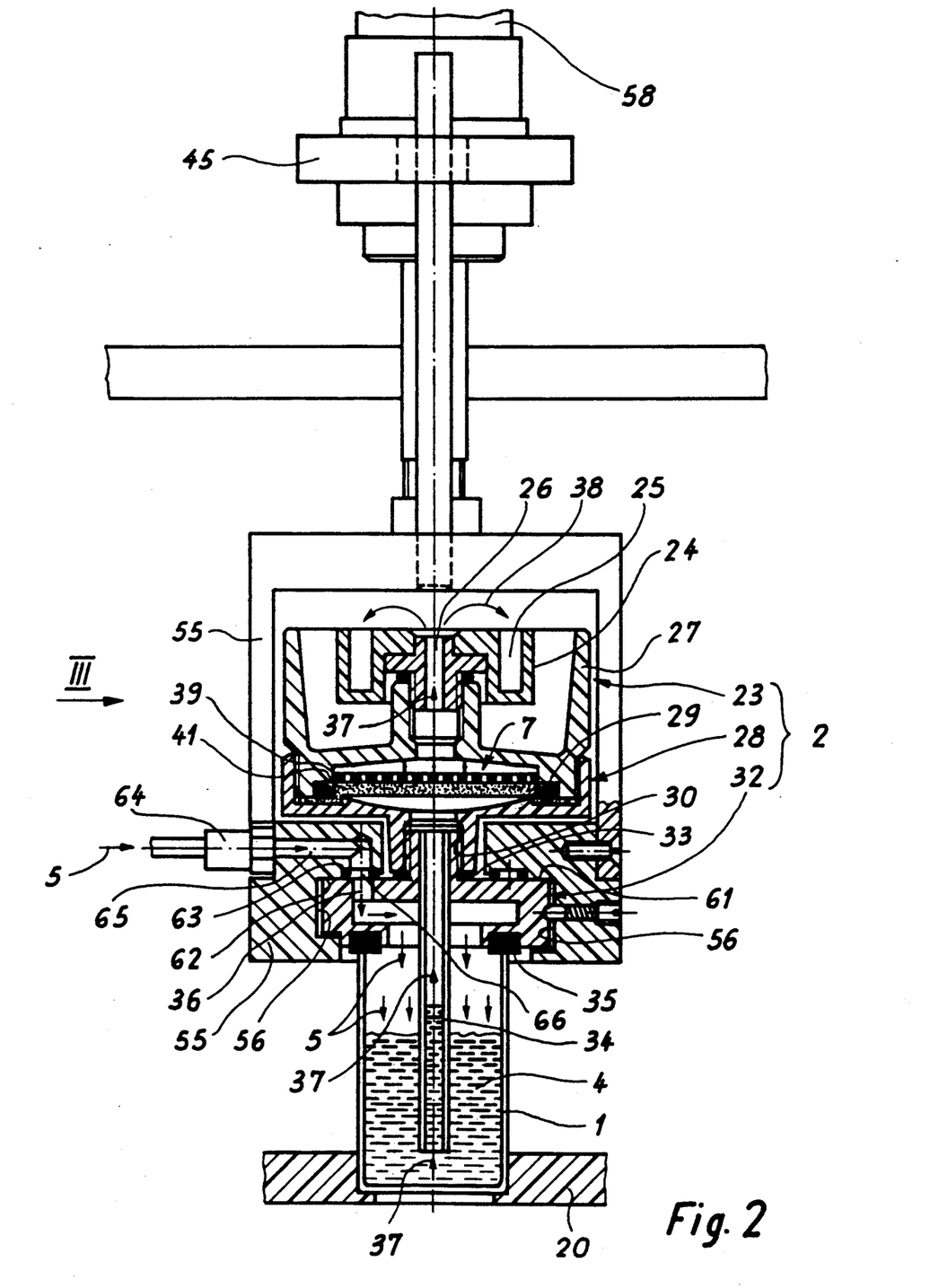
FIG. 2 is a front elevation view partially cut away of the filtering arrangement according to the invention corresponding to FIGS. 1a to 1e.
Figure 3:
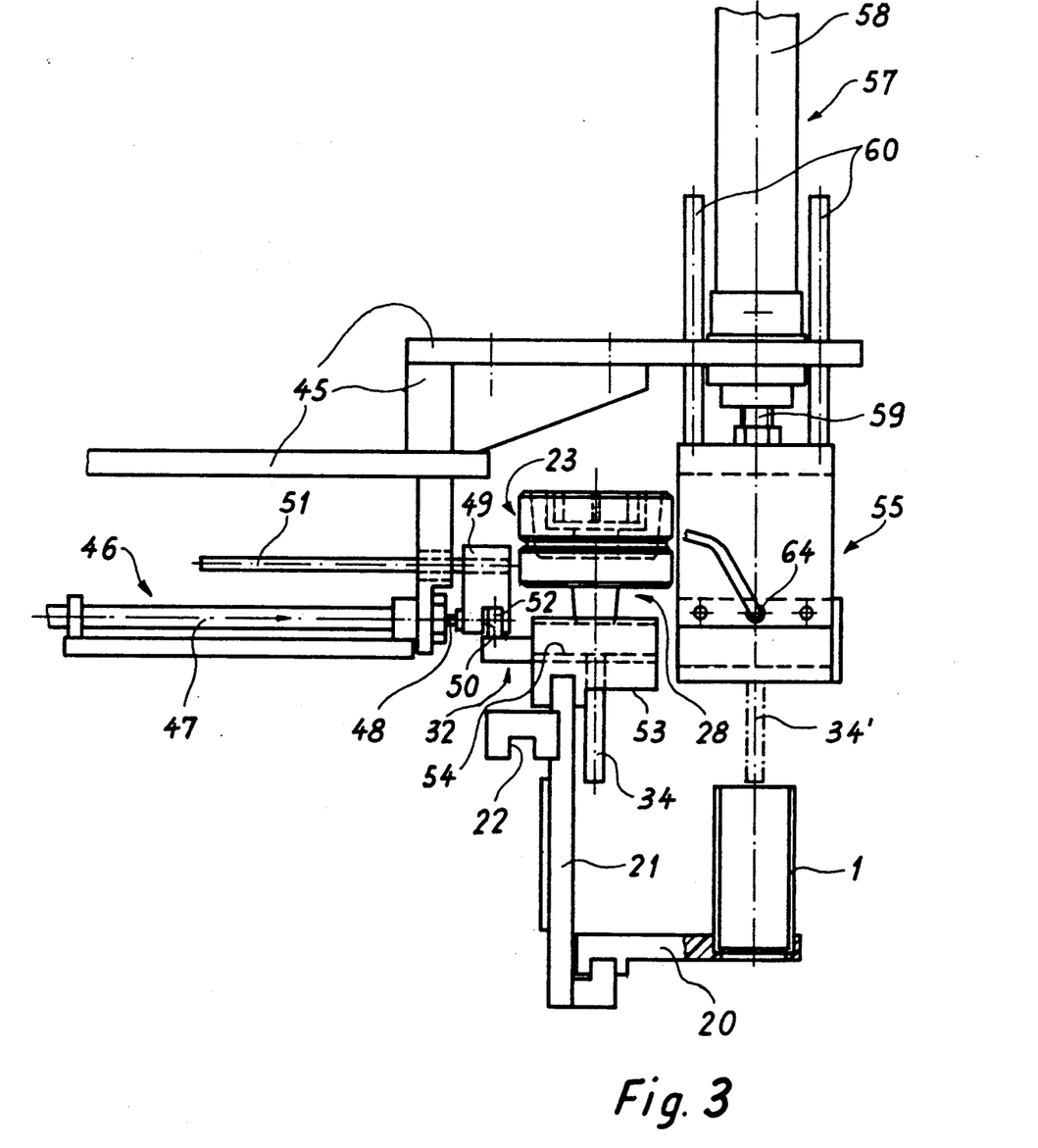
FIG. 3 is a lateral elevation taken along the arrow III of FIG. 2, the elements composing the arrangement being represented in relatively different positions.

FIG. 2 is a front elevation, partially in cross-section, of the filtering post according to the invention, and FIG. 3, a lateral elevation in the direction of arrow III of FIG. 2, the elements comprising this station being shown in different relative positions. At this station are effected the operations which have been described having reference to FIGS. 1a to 1e. These figures show that the filtering station includes a first recipient 1 containing the liquid sample to be filtered 4, this sample being increased by an excess quantity relative to the volume of the desired sample. This first recipient 1 is placed in a cell of a support 20, itself fixed to a carrier 21 provided with a slide 22 which may be displaced along a rail not shown. This work station also includes a second recipient 2 which comprises on one hand decanting means for the liquid from the first to the second recipient and on the other hand filtering means interposed along the path over which the decanting is carried out. Support 20 further comprises a third recipient which is not shown on FIGS. 2 and 3. The position of the third recipient relative to the second appears on the other hand on figure 5 which will be discussed subsequently.

There will now be described in detail having reference to FIG. 2, a preferred embodiment of the second recipient 2. This recipient includes initially an upper element 23 having a cylindrical block 24 in which is provided an annular chamber 25 intended to receive liquid 4 decanted from the first recipient 1. At the center of the cylindrical block 24 there is pierced an axial duct 26. The cylindrical block is surrounded by a bowl 27, to receive excess liquid which may run over from chamber 25. The second recipient 2 further includes an intermediate element 28 fitted to the upper element 23 by means of a first seal 29. This intermediate element shows on its lower portion an opening 30 aligned with the axial duct 26 of the upper element 23. A filtration chamber 7 is interposed between the upper and intermediate elements. Finally, the second recipient 2 includes a lower element 32 fitted to the intermediate element 28 by means of a second seal 33. A nozzle 34 projects from the lower portion of lower element 32, such nozzle being aligned with the opening 30 of the intermediate element. As is seen on FIG. 2, the lower element 32 further includes a third seal 35 which is applied to the rim of the first recipient 1 during the decanting. The lower element further has a channel 36 through which may be injected compressed air. As shown by arrows 5 on the figure, this compressed air acts on the contents 4 of the recipient and drives the liquid therein by the path indicated by arrows 37, such path consisting successively of the nozzle 34, the opening 30, the filtration chamber 7 and finally the axial duct 26. The liquid then fills the annular chamber 25 following the path indicated by arrows 38.

The fitting of the three elements as described may be obtained in various manners. Herein the elements are screwed onto one another. The upper chamber 23 has been described as a unit in itself. Actually, the figure shows that the cylindrical block 24 is likewise screwed to the bowl 27, a seal being arranged between these two members.

As far as the filtration chamber is concerned, figure 2 shows that said chamber includes a grid 39 forming part of the upper element 23 and that a filter 41 (porous paper for instance) is arranged against said grid at the same time that it is squeezed under the first seal 29.

The first filtration station will now be explained having reference to FIG. 3. The station comprises a chassis 45 which supports first motor means 46 comprising in the preferred embodiment a pneumatic thruster 47 the mobile stem 48 of which is fastened to an element 49 provided with a groove 50. Element 49 is guided in its rectilinear movements by means of guides 51 cooperating with the chassis 45. The lower element 32 of the second recipient is provided with a stud 52 cooperating with the groove 50 by means of which said second recipient may be horizontally displaced from a first withdrawn position—that shown on FIG. 3—to a second position wherein its nozzle 34' is located in line with the opening presented by the first recipient 1. In the withdrawn position the lower element 52 of the second recipient rests in an element 53 provided with grooves 54 between which this lower element 32 may slide. The element 53 is itself fixed to the carrier 21. When the thruster 47 is actuated, the second recipient is pushed towards the right of the figure, comes out of element 53 and engages in gripping means 55. As may be seen on FIG. 2, the lower portion of this gripping means or clamp 55 is likewise provided with sliders 56 in which the lower element 32 of the second recipient 2 may be engaged. When the second recipient is pushed to the limit within the clamp 55, it is liberated from the element 53 forming part of the carrier 21 and may thus move vertically as will now be explained.

FIG. 3 shows that the chassis 45 bears second motor means 57 including a pneumatic thruster 58 of which the moving stem 59 is fixed to the clamp 55. Guides 60 prevent any rotation of the clamp during its displacement. When the thruster 58 is actuated, the clamp 55 descends vertically until the third seal 35 of the lower element 32 of the second recipient 2 comes in contact with the rim of the first recipient 1 (situation shown on FIG. 2). From this moment the decanting may take place.

During the decanting, the thruster continues to be actuated to assure initially a good application of the seal 35 against the rim of recipient 1. The force applied onto recipient 1 has as effect finally to cause adhesion of the upper portion 61 of the lower element 32 against the top 62 of the slider 56 provided in the clamp and this action compresses a fourth seal 63, the utility of which will now appear.

FIG. 2 shows that the clamp 55 comprises a nipple 64 connected to a compressed air supply 5. This nipple is provided with a conduit 65 arranged within the clamp. The end of the conduit 65 exhibits an orifice 66 which corresponds to the entry of duct 36 provided in the lower element 32 of the second recipient 2, this correspondence being brought about through the design when the recipient 2 is introduced as far as possible into the clamp 55. The fourth seal 63 being interposed between orifice 66 and conduit 65 and the input of duct 36 and being compressed by the force applied by the thruster, there results a flow without loss of the compressed air employed for driving the liquid out of the first recipient.

There will preferably be employed to drive the thruster 58 the same pressure of compressed air 5 as that employed for driving the liquid 4 from the first recipient 1. Under these conditions, if one chooses for the thruster 58 a piston diameter which is greater than the interior diameter of the first recipient, it will be understood that the force exerted by the second recipient 25 onto the first via the third seal 35 will at all times be greater than the force exerted on the liquid 4 and which tends to lift clamp 55. One is thus at all times assured of a good application of the two recipients onto one another as well as good sealing of the path followed by the compressed air.

As soon as the quantity of filtered liquid has been decanted into the second recipient, this same recipient follows a path opposite to that described hereinabove: the clamp 55 is lifted by operating the thruster 58 and the second recipient 2 is brought back to its withdrawn position by means of the thruster 47. One then finds the situation shown on FIG. 3. At this moment the carrier 21 is advanced to the next station, for instance in front of the plane of FIG. 3. The second recipient then is disengaged from the retention of thruster 47 since the stud 52 slides outside slot 50. Carrier 21 provided with its same three recipients 1, 2 and 3, is then in front of the second metering station which will now be explained.

Figure 4:
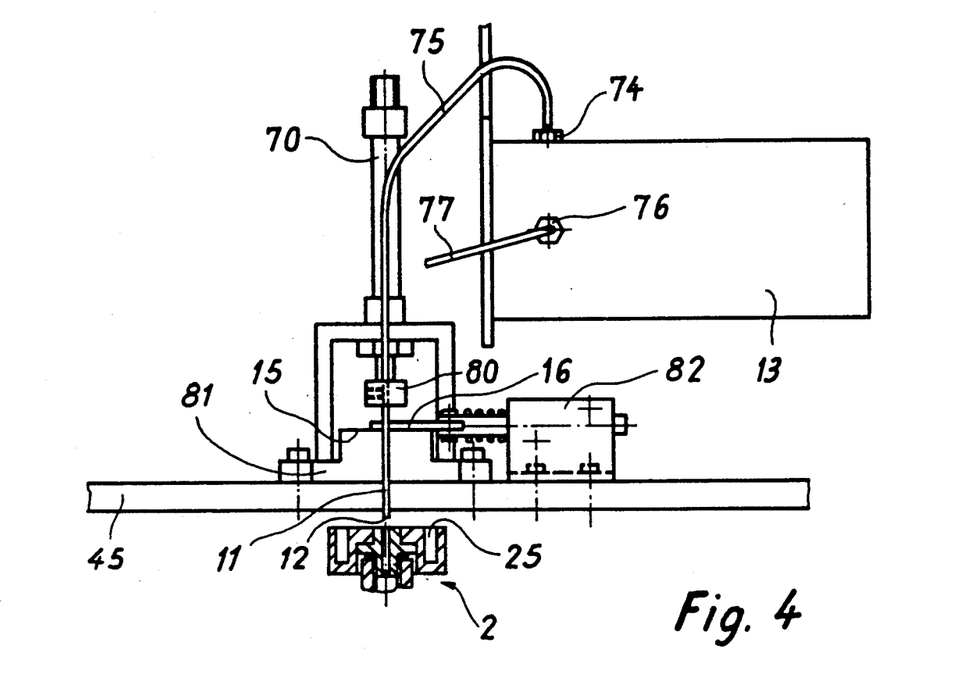
FIG. 4 is a front elevation partially cut away of the metering arrangement according to the invention corresponding to FIGS. 1f to 1i.
Figure 5:
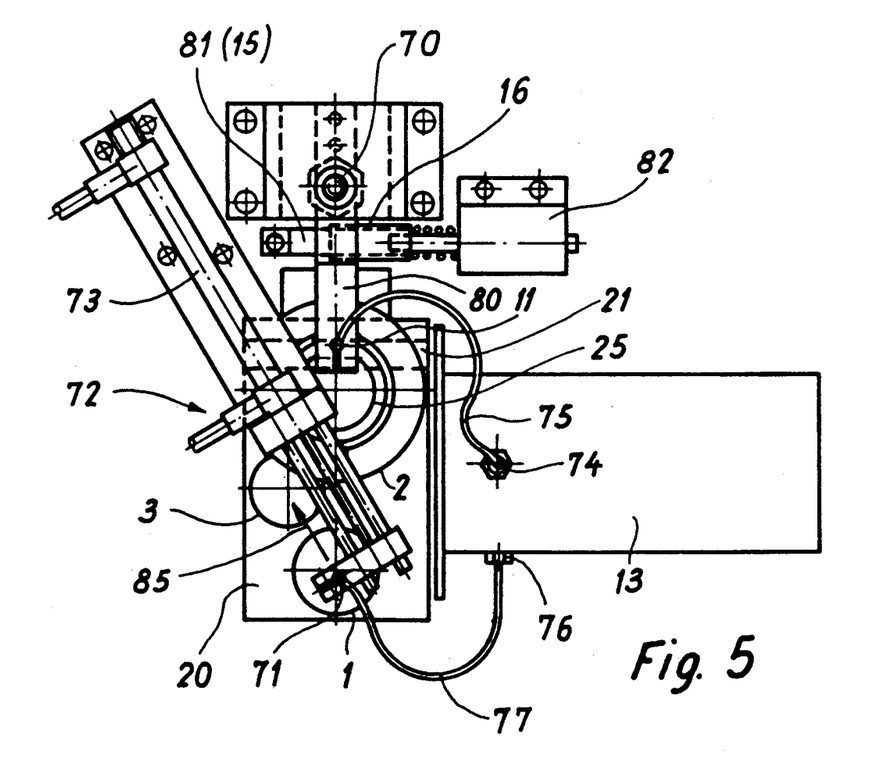
FIG. 5 is a top view of FIG. 4.

FIG. 4 is a front elevation view, partially cut away, of the metering station according to the invention and FIG. 5 a top view of FIG. 4. At this station are brought about the operations which have been described having reference to FIGS. 1f to 1i.

FIG. 5 shows the two recipients 1 and 3 arranged on their common support 20 as well as the recipient 2 fixed to the carrier 21. Into the annular chamber 25 of the recipient 2 is arranged to be plunged a first pipette 11 as is better seen on FIG. 4. This pipette may be vertically displaced by motor means which may consist of a pneumatic thruster 70. This thruster permits the positioning of the orifice 12 of the pipette 11 initially in a first position where it is outside recipient 2 (situation shown on FIGS. 1f and 4), next in a second position where it is plunged into the liquid to a first level A (situation shown on FIG. 1g), finally into a third position where it is plunged into the liquid to a second level B below the first (situation shown by FIG. 1f), this in response to metering means of which an embodiment will be examined in detail hereinafter.

FIG. 5 also shows a second pipette 71 capable of being initially aligned with the first recipient 1 then aligned with the third recipient 3 following the path indicated by arrow 85, this being responsive to horizontal displacement means 72 operated for instance by the pneumatic thruster 73. It will here be observed that the horizontal means of displacement 72 are not shown on FIG. 4 in order not to overcharge and complicate the drawing.

A pump 13, for instance a peristaltic pump, is provided for decanting the liquid from the second recipient 2 into one or the other of recipients 1 and 3. To bring this about, the pump intake is coupled to the first pipette 11 by the flexible tube 75 and the discharge 76 of said pump is coupled to the second pipette 71 by the flexible tube 77.

Control means not shown and which may comprise the computer mentioned hereinabove, with its associated interfaces, coordinate the movements of this displacement means in order to pour into the first recipient 1 the liquid located above the first level A of the second recipient 2 and into the third recipient 3 the liquid located between the first and second levels A and B respectively of the same second recipient 2. The third recipient then will contain the desired metered volume of liquid.

As soon as the desired volume of liquid has been obtained, the carrier is disengaged from the station which has just been discussed. Recipient 3 may then be passed to a new work station where for instance the pH of its liquid may be adjusted (procedure of ATP treatment mentioned hereinabove). The purpose to be attained could however be different. For instance the metered liquid could in the new work station simply be weighed.

There remains to be described a metering method according to a preferred embodiment of the invention. FIGS. 4 and 5 show that the first pipette 11 is borne on a cross bar 80. This crossbar may butt against a reference plane 15 provided by a piece 81 fixed to the machine framework 45. In this situation shown schematically on FIG 1i, the orifice 12 of the pipette 11 is located in its third position corresponding to the level B of the liquid.

FIGS. 4 and 5 show that on the framework 45 of the machine are mounted displacement means (for instance electromagnet 82) of a shim 16. This shim may be added to the reference plane 15 as is well shown on FIG. 4. When the shim 16 is interposed between the crossbar 80 and the plane 15, the crossbar will butt against the shim and the orifice 12 of the pipette 11 is then located in the second position corresponding to the level A of the liquid. Thus, in this embodiment, the thickness of the shim is proportional to the desired volume of liquid.

The method and the arrangement for its implementation concern, in the preceding description, two successive work stations: filtration and metering.

Should the liquid not require filtering, but simply metering, one could remove the filter paper 41 from the second recipient 2 and bring about the decanting from the first to the second recipient as indicated hereinabove at the first work station, or eliminate the first station and suck the metered liquid directly into the first recipient. In this latter case, however, it would be necessary to provide on support 20 a supplementary recipient which would serve for discharge.

If on the other hand the liquid does not require to be metered, but simply filtered, one may simply eliminate the second metering station.

What we claim is:

1. Method of filtering and metering a liquid sample comprising the steps of provided a first recipient in which is placed the sample to be filtered and metered, the volume of the sample comprising the desired quantity plus an excess, providing a second recipient into which is decanted the sample contained in the first recipient, the volume decanted likewise comprising the desired quantity plus an excess, interposing filtering means between the first and second recipients, decanting into the first recipient a quantity of sample less than the excess quantity in the second recipient, providing a third recipient into which is decanted from the second recipient the desired quantity of the liquid samples.

2. A method as set forth in claim 1 in which the sample is decanted from the first to the second recipient by means of compressed air.

3. A method as set forth in claim 1 comprising the further steps of plunging a pipette into the liquid of the second recipient and sucking up the liquid down to a first level corresponding to that of the pipette orifice so as to decant into the first recipient a quantity of liquid less than the excess quantity contained in the second recipient, lowering the orifice of said pipette to a second level below the first level, sucking up the liquid contained between the two levels until the lower level is attained and decanting said liquid into the third recipient, the volume of liquid contained between said first and second levels corresponding to the desired quantity of liquid sample.

4. An arrangement for filtering and metering a liquid sample including a first filtering station comprising a first recipient containing a desired volume of the liquid sample to be filtered and metered plus an excess quantity thereof, a second recipient further including means for decanting the sample into said second recipient and filtering means interposed in the decanting means, a second metering station located after said first filtering station, and a third recipient, said second metering station comprising pumping means for initially discharging into the first recipient a certain quantity of liquid from the second recipient and subsequently discharging into the third recipient a predetermined quantity of liquid from the second recipient corresponding to the desired volume in response to metering means arranged in the second station, wherein the second recipient comprises an upper element including a cylindrical block in which is formed an annular chamber intended to receive the decanted liquid, a bowl surrounding the cylindrical block arranged to receive liquid overflow from the chamber and an axial duct piercing said cylindrical block, an intermediate element fitted to the upper element by means of a first seal, said intermediate element having on its lower portion an opening aligned with the axial duct of the upper element, a filter chamber being interposed between said upper and intermediate elements and a lower element fitted to the intermediate element by means of a second seal, said lower element exhibiting a nozzle projecting from its lower portion, said nozzle being aligned with the opening of the intermediate element, said lower element further including a third seal adapted to be applied to the rim of the first recipient during decanting of liquid from the first to the second recipient and a duct through which compressed air may be injected in order to decant the liquid from the first to the second recipient, said liquid following a decanting circuit formed successively by the nozzle of the lower element, the opening of the intermediate element, the filter chamber and the axial duct of the upper element.

5. An arrangement as set forth in claim 4, wherein the filter chamber includes a grid forming part of the upper element and a filter arranged against said grid.

6. An arrangement as set forth in claim 4 wherein the first filtering station includes first motor means for effecting displacement of the second recipient in a horizontal plane from a first withdrawn position to a second position where its duct is aligned with the orifice of the first recipient, grasping means for said second recipient when located in said second position and second motor means acting on said grasping means so as to displace said second recipient in a vertical plane and to bring it to a third position in which the third seal is applied to the rim of the first recipient.

7. An arrangement as set forth in claim 6 wherein the grasping means comprises a nipple connected to a compressed air supply, a conduit formed within said grasping means and connected to the nipple, the conduit having an orifice corresponding to the duct provided in the lower element of the second recipient, a fourth seal arranged between the orifice of the conduit and the duct entry, said fourth seal being compressed when the second recipient is applied to the first.

8. An arrangement for filtering and metering a liquid sample including a first filtering station comprising a first recipient containing a desired volume of the liquid sample to be filtered and metered plus an excess quantity thereof, a second recipient further including means for decanting the sample into said second recipient and filtering means interposed in the decanting means, a second metering station located after said first filtering station, and a third recipient, said second metering station comprising pumping means for initially discharging into the first recipient a certain quantity of liquid from the second recipient and subsequently discharging into the third recipient a predetermined quantity of liquid from the second recipient corresponding to the desired volume in response to metering means arranged in the second station, wherein the second metering station includes a first pipette adapted to be plunged into the second recipient, means for vertically displacing said first pipette arranged to position its orifice initially in a first position outside the recipient, then to a second position when it plunges into the liquid to a first level and finally to a third position in which it plunges to a second level below the first, said second and third positions being determined by metering means, a second pipette, horizontal displacement means for said second pipette, said second pipette adapted to be aligned initially with the first recipient and then with the third recipient in response to said horizontal displacement means, a pump the intake and discharge of which are respectively coupled to the first and second pipettes and control means for said vertical and horizontal displacement means thereby to decant into said first recipient the liquid above the first level of the second recipient and into the third recipient the liquid between the first and second levels of the second recipient, the volume of such liquid corresponding to the desired volume.

9. An arrangement as set forth in claim 8 wherein the first pipette is borne by a crossbar which comes to butt against a reference plane when the orifice of said pipette arrives in the third position and wherein the metering means consist in the placing of a regulating shim on the reference plane in a manner such that when the shim is added the crossbar butts against it, the orifice of the first pipette then being in its second position, the thickness of the shim being proportional to the desired volume of liquid.

* * * * *